May 29, 1962 F. B. BEGONIA ETAL Plant Pat. 2,150
ROSE PLANT
Filed July 7, 1961
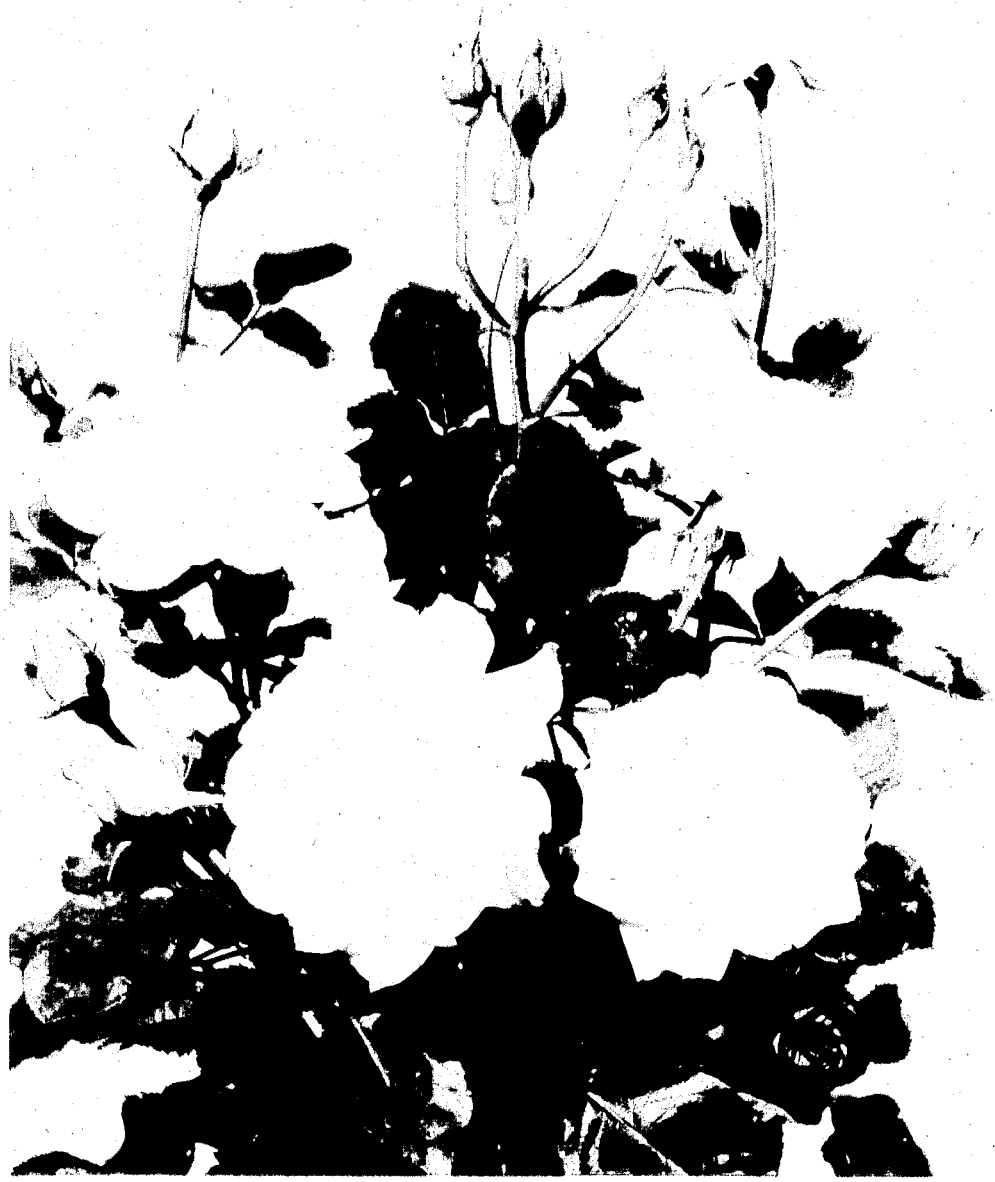
Inventors.
F. B. Begonia
P. F. De Vor
By: Robb & Robb
Attorneys.

United States Patent Office

Plant Pat. 2,150
Patented May 29, 1962

2,150
ROSE PLANT

Francisco B. Begonia and Paul F. De Vor, Livermore, Calif., assignors, by mesne assignments, to Armstrong Nurseries, Inc., Ontario, Calif., a corporation of California Filed July 7, 1961, Ser. No. 122,601
1 Claim. (Cl. 47—61)

The present invention relates to a new and distinct variety of rose plant of the floribunda class, which was discovered by us as a cultivated sport of the variety "Circus" (Plant Patent No. 1,382).

At the time of our discovery aforementioned, we were engaged in the growing of a large number of plants of the parent variety "Circus," which were planted in the fields of our assignee, said fields being located at Livermore, California. In the course of our cultivation and inspection of these fields, our attention was attracted to one particular plant amongst those of the variety "Circus" by the fact that this plant exhibited a somewhat more vigorous habit of growth, and also bore flowers which appeared to have a greater over-all richness of color and more red color therein. Upon closer examination of this plant, we found that it had sported, and we thereupon took steps to preserve the sport, keep it under observation, and later asexually reproduce the same. Our continued observations of the original plant and the asexually reproduced progeny thereof, as produced by budding at Livermore, California, fully confirmed the new characteristics referred to in the foregoing, as well as established the existence of other important and desirable characteristics which, altogether, represent a new and unique combination of features which differentiate the new sport from its parent variety, as well as from all other varieties of which we are aware. The outstanding features of this new combination are as follows:

(1) A somewhat more vigorous habit of growth than that of the parent variety "Circus";

(2) A bud form which is generally quite attractive and urn-shaped, comparable to that of the buds of the parent variety "Circus," but having a greater tendency to distortion of the bud form by blunting, at least in southern California;

(3) Substantially more red color in the flowers than in those of the parent variety "Circus," thus giving to the flowers an appearance of a redder and more rich color of the multi-colored type in which the yellow colors also appear to be emphasized and enhanced, even though there may not be much, if any, actual increase of the yellow color itself; and (4) A greater resistance to fading of the flower color, particularly during the warmer part of the growing season and under soil conditions which sometimes causes fading of the flowers of the parent variety "Circus."

Other than the differences noted in the foregoing, the new sport is substantially identical to that of its parent variety "Circus."

The accompanying drawing shows typical specimens of the flowers and foliage of our new variety in different stages of development and as depicted in color as nearly true as it is reasonably possible to make the same in a color illustration of this character.

In view of the similarities between the new variety and its parent, excepting for the principal features noted above, it is unnecessary to describe the new variety in complete detail, since it generally conforms to the description appearing in Plant Patent No. 1,382, issued April 19, 1955, to which reference may be readily had. However, for convenience, the following description is given of the flower colors and other basic details of the new variety with color terminology in accordance with Robert F. Wilson's Horticultural Colour Chart:

Type: Bush; outdoor; sport; for cut flowers and for garden decoration.

Class: Floribunda.

Parentage: Sport of "Circus."

Propagation: Holds its distinguishing characteristics through succeeding propagations by budding.

*Flower*

(Observations made from specimens grown at Ontario, California.)

Bud:

*As calyx breaks.*—Color—near Burnt Orange, Plate 014/2, page 105, with areas exposed longer to light near Oxblood Red, Plate 00823/2, page 191.

*As first petal opens.*—Color: outside—between Orange, Plate 12/1, age 12, and Saturn Red, Plate 13/1, page 13, overlaid with near Geranium Lake, Plate 20/1, page 20, and with area at base of petal near attachment near Buttercup Yellow, Plate 5/2, page 5; inside—between Orange, Plate 12/1, page 12, and Saturn Red, Plate 13/1, page 13, overlaid with near Geranium Lake, Plate 20/1, page 20, and with area at base of petal near attachment near Buttercup Yellow, Plate 5/2, page 5.

This description of a newly opened flower was made from a rose grown outdoors during the month of November at Ontario, California:

*Color.*—Outer petal: outside surface—between Saffron Yellow, Plate 7/2, page 7 and Cadmium Orange, Plate 8/2, page 8, overlaid with near Carmine, Plate 21/1, page 21, and with small area at base of petal near attachment near Aureolin, Plate 3/1, page 3; inside surface—between Cadmium Orange, Plate 8/2, page 8, and Tangerine Orange, Plate 9/2, page 9, overlaid slightly with near Carmine, Plate 21/1, page 21, and with area at base of petal near attachment near Aureolin, Plate 3/1, page 3. Intermediate petal: outside surface—between Indian Yellow, Plate 6/3, page 6, and Saffron Yellow, Plate 7/3, page 7, blending with near Aureolin, Plate 3/2, page 3 toward base of petal, with area near apex of petal very lightly overlaid with near Geranium Lake, Plate 20/3, page 20; inside surface—near Saffron Yellow, Plate 7/2, page 7, blending with near Aureolin, Plate 3, page 3 toward base of petal, with area at apex of petal slightly overlaid with near Geranium Lake, Plate 20/2, page 20. Inner petal: outside surface—between Indian Yellow, Plate 6/3, page 6, and Saffron Yellow, Plate 7/3, page 7, blending with near Aureolin, Plate 3/2, page 3 toward base of petal, with area near apex of petal very lightly overlaid with near Geranium Lake, Plate 20/3, page 20; inside surface—near Saffron Yellow, Plate 7/2, page 7, blending with near Aureolin, Plate 3, page 3 toward base of petal, with area at apex of petal slightly overlaid with near Geranium Lake, Plate 20/2, page 20.

This description was made from a rose that was open for three days outdoors during the month of November at Ontario, California:

*Color.*—Outer petal: outside surface—between Indian Yellow, Plate 6/2, page 6 and Saffron Yellow, Plate 7/3, page 7, blending with near Aureolin, Plate 3/2, page 3 toward base of petal, with upper ½ to ⅔ of petal overlaid with between Carmine, Plate 21/2, page 21 and Crimson, Plate 22/2, page 22; inside surface—between Buttercup Yellow, Plate 5/2, page 5 and Indian Yellow, Plate 6/2, page 6, blending with near Aureolin, Plate 3/1, page 3 toward base of petal, and overlaid with near Crimson, Plate 22/2, page 22 on upper ½ to ⅔ of petal. Inner petal: outside surface—between Lemon Yellow, Plate 4/2, page 4 and Buttercup Yellow, Plate 5/2, page 5, overlaid somewhat, particularly on upper portions of petal near margins with near Crimson, Plate 22/3, page 22, and with small area at base of petal near attachment near Aureolin, Plate 3/2, page 3; inside surface—between Lemon Yellow, Plate 4/2, page 4 and Buttercup Yellow, Plate 5/2, page 5, heavily overlaid with near Carmine, Plate 21/1, page 21 on upper ½ to ⅔ of petal, and with small area at base of petal near attachment near Aureolin, Plate 3/2, page 3.

*General color effect.*—Newly opened flower—between Saffron Yellow, Plate 7/2, page 7 and Saturn Red, Plate 13/2, page 13. 3-days open—between Saturn Red, Plate 13/3, page 13 and Geranium Lake, Plate 20/1, page 20. Older flowers (more than 3 days open)—usually have color between Vermilion, Plate 18/3, page 18 and Tyrian Rose, Plate 24/2, page 24.

We claim:

A new and distinct variety of rose plant of the floribunda class, substantially as herein shown and described, characterized particularly as to novelty by being generally similar to its parent variety "Circus" (Plant Patent No. 1,382), but being essentially distinguished therefrom by a somewhat more vigorous habit of growth, an attractive and generally urn-shaped bud form which has a somewhat greater tendency toward blunting of the buds, substantially more red color in the flowers and greater emphasis of the yellow colors even without actual increase of yellow pigmentation with consequent greater over-all richness of the flower color, and a greater resistance of the flowers to fading, particularly during warm weather, with consequent maintenance of a brighter multi-colored effect than the flowers of "Circus."

No references cited.